(12) United States Patent
Lemmens et al.

(10) Patent No.: US 6,686,473 B2
(45) Date of Patent: Feb. 3, 2004

(54) PROCESS FOR THE PRODUCTION OF PAROXETINE

(75) Inventors: Jacobus M. Lemmens, Mook (NL); Theodorus H. A. Peters, Arnhem (NL); Frantisek Picha, Brno (CZ)

(73) Assignee: Synthon BCT Technologies, LLC, Chapel Hill, NC (US)

( * ) Notice: Subject to any disclaimer, the term of this patent is extended or adjusted under 35 U.S.C. 154(b) by 0 days.

(21) Appl. No.: 10/076,221

(22) Filed: Feb. 15, 2002

(65) Prior Publication Data

US 2002/0151716 A1 Oct. 17, 2002

(30) Foreign Application Priority Data

Feb. 21, 2001 (NL) .............................................. 1017421

(51) Int. Cl.$^7$ ............................................. C07D 405/12
(52) U.S. Cl. ........................ 546/197; 546/198; 546/205; 546/236; 514/317; 514/319; 514/320
(58) Field of Search ................................ 546/197, 198, 546/205, 236; 514/317, 319, 321

(56) References Cited

U.S. PATENT DOCUMENTS

| 4,007,196 A | 2/1977 | Christensen et al. ........ 546/197 |
| 4,721,723 A | 1/1988 | Barnes et al. ................ 546/197 |
| 5,874,447 A | * 2/1999 | Benneker ..................... 517/321 |

FOREIGN PATENT DOCUMENTS

| EP | 0152273 B1 | | 8/1985 |
| EP | 190496 | * | 8/1986 |
| EP | 0190496 A2 | | 8/1986 |
| EP | 0223403 B1 | | 8/1993 |
| EP | 0810225 B1 | | 8/2001 |
| GB | 2297550 | * | 8/1996 |
| GB | 2336364 A | | 10/1999 |
| JP | 2000-95780 | * | 4/2000 |
| WO | WO 9932484 | | 7/1999 |
| WO | WO 9952901 | | 10/1999 |
| WO | WO 0032594 | | 6/2000 |
| WO | WO 0039090 | | 7/2000 |
| WO | WO0078753 A1 | | 12/2000 |

* cited by examiner

Primary Examiner—Ceila Chang
(74) Attorney, Agent, or Firm—Mark R. Buscher

(57) ABSTRACT

The synthesis of paroxetine can be made more convenient by using a solvent system comprising an aliphatic alcohol and a hydrocarbon co-solvent. The solvent system is used particularly in the hydrolysis of paroxetine phenylcarbamate and preferably uses butanol and toluene as the system.

20 Claims, No Drawings

PROCESS FOR THE PRODUCTION OF PAROXETINE

This application claims the benefit of priority under 35 U.S.C. §119 from The Netherlands patent application serial number 1017421, filed Feb. 21, 2001, the entire contents of which are incorporated herein by reference.

BACKGROUND OF THE INVENTION

The present invention relates to a process for preparing the pharmaceutically active compound paroxetine.

Pharmaceutical products with antidepressant and anti-Parkinson properties are described in U.S. Pat. No. 4,007,196. An especially important compound is paroxetine, the (−) trans isomer of 4-(p-fluorophenyl)-3-(3,4-methylenedioxy-phenoxymethyl)-piperidine of the formula (1).

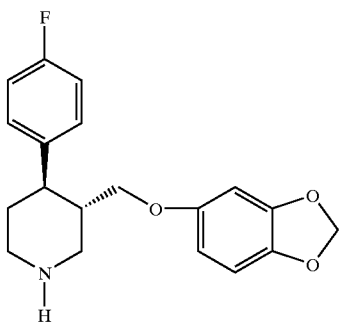
(1)

The compound has been used in therapy as the hydrochloride hemihydrate salt to treat e.g. depression, obsessive compulsive disorder and panic.

U.S. Pat. No. 4,007,196 discloses the formation of paroxetine by the demethylation of N-methylparoxetine of the formula (2):

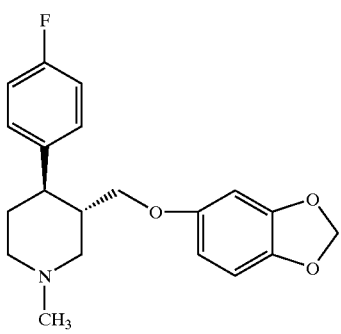
(2)

via a paroxetine phenylcarbamate intermediate of the formula (3).

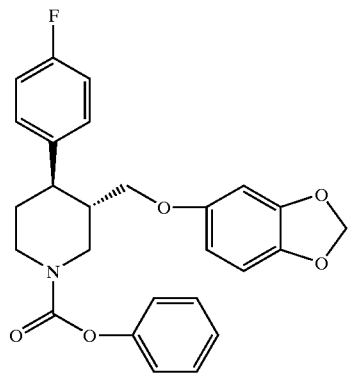
(3)

The paroxetine phenylcarbamate is subsequently hydrolyzed to paroxetine in an appropriate solvent. Specifically, the formation of the paroxetine phenylcarbamate (3) is formed by a reaction of N-methylparoxetine with phenyl chloroformate in dichloromethane at 0° C.–5° C. The solution after reaction was washed with aqueous NaOH and HCl and evaporated. A solid mixture was obtained which was suspended in benzene, filtered and evaporated again. The evaporation residue (i.e. the crude phenylcarbamate (3)) was refluxed with solid KOH in methylcellosolve (2-methoxyethanol) for 4 hours. The obtained solution of paroxetine was evaporated, whereby the residue after evaporation was subjected to water/benzene extraction and paroxetine was isolated from the benzene layer as the maleate salt.

EP152273 discloses a similar process wherein phenylcarbamate of a paroxetine analogue was prepared from the N-methylated precursor in toluene, isolated and purified by recrystallization from ethanol, and the solid phenylcarbamate product hydrolyzed to the desired paroxetine analogue by solid KOH under 2–4 hours reflux in 2-methoxyethanol. The remainder of KOH and water soluble by-products were removed from the reaction mixture by adding a mixture of water and toluene to the reaction mixture and removal of the aqueous layer. The toluene layer contained the desired product.

In EP 190496, a solid-state phenylcarbamate (3) was hydrolysed by KOH in 2-methoxyethanol. The KOH was added at 60° C. for a period of one hour whereafter the mixture was heated to reflux for 2.5 hours. The crude mixture was treated with water and the product was extracted into toluene.

A common procedure is disclosed in EP223403, and corresponding U.S. Pat. No. 4,721,723, wherein a solid-state paroxetine phenylcarbamate (3) was dissolved in toluene and KOH was added. The mixture was refluxed for 2 hours with good agitation. The slurry was then cooled to 20° C. and the toluene washed with water. The obtained solution of paroxetine free base in toluene was further treated with HCl to isolate paroxetine in a form of its hydrochloride salt. Similar procedures for the synthesis of paroxetine and various salts of paroxetine have been disclosed in WO 99-32484, GB 2336364, WO 99-52901, WO 00-39090 and WO 00-32594.

However, WO 00-78753 reports that the above described processes suffer from several disadvantages. Specifically, the use of 2-methoxyethanol produces an undesired trans-esterified intermediate that is slow to hydrolyze and that leaves a residue that is difficult to remove from the hydrolyzed product. Alternatively, the method disclosed in EP 223403, in which no 2-methoxyethanol was used, could not be easily scaled up; long and/or incomplete reactions were encountered. Apparently, the KOH melts at the toluene reflux temperature and can react with carbamate derivatives to form an insoluble complex mass. If this mass forms, complete reaction is not possible and reactor clean up is difficult.

To overcome these disadvantages, WO 00-78753 discloses an improved method of hydrolysis of the solid-state paroxetine phenylcarbamate that comprises forming a complex of KOH and carbamate derivative in toluene, but below the reflux temperature. The complex is sand-like and is easily stirrable. The well-stirred mixture or suspension is then further heated to complete the hydrolytic reaction.

But this method suffers from the need to carefully control the reaction conditions to obtain the desired finely divided suspension instead of the insoluble complex mass. The suspension is only temporarily formed at a certain temperature which should be maintained for a certain time to complete the formation. Further, the process requires slow and step-wise heating and vigorous stirring. If these conditions are not met, e.g. if the reaction mixture is overheated, the same problems as reported for the other toluene based hydrolysis techniques are likely to occur.

EP 810 225 discloses the preparation of paroxetine by a similar demethylation and hydrolysis procedure but using carbamate derivatives other than phenylcarbamate. Example 1 shows the hydrolysis of an ethoxycarbamate derivative using KOH in a mixture of toluene and ethanol at reflux, while example 3 uses ethanol as the only solvent. However, these reactions took two days and three days, respectively. Thus, scale up of the teachings in EP 810 225 seems difficult and/or not commercially justifiable.

It would be desirable to have a more convenient process for making paroxetine. It would further be desirable to provide a process that eliminated or reduced the need to use liquid-solid suspension reaction systems.

SUMMARY OF THE INVENTION

The present invention relates to a process for making paroxetine wherein the solvent system provides for improved operating ease. Accordingly, a first aspect the present invention provides a process for the production of paroxetine, which comprises hydrolyzing a paroxetine phenylcarbamate of formula (3)

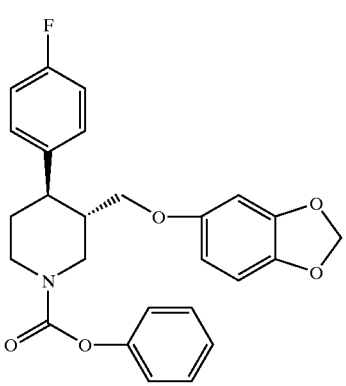

(3)

with a hydrolyzing agent in a solvent system comprising an aliphatic alcohol and a hydrocarbon co-solvent, to form a paroxetine compound of formula (1).

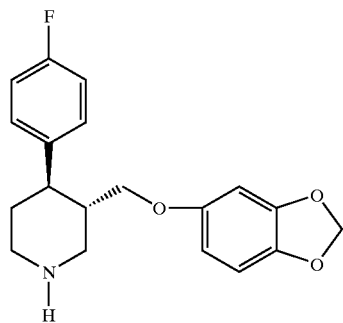

(1)

The aliphatic alcohol preferably has a boiling point in the range of about 70° C. to about 150° C., such as ethanol, propanol, isopropanol, 1-butanol, 2-butanol, or tertiary butanol; most preferably 1-butanol. The hydrocarbon solvent is typically benzene, toluene, xylene or cyclohexane, and preferably is toluene.

The hydrolysis of paroxetine phenylcarbamate to paroxetine according to the present invention enables the reaction to be carried out in an easily controllable, robust and reproducible manner in industrial scale.

DETAILED DESCRIPTION OF THE INVENTION

The present invention relates to the discovery that a solvent system comprised of a non-hydrocarbon solvent and a hydrocarbon co-solvent, preferably wherein the solvent and the co-solvent are at least partly miscible, can be formed that will more easily handle the hydrolysis of paroxetine phenylcarbamate. It has now been discovered that alkanols derived from alkane hydrocarbons do not exhibit the above reported disadvantages associated with structurally related methyl cellosolve. For clarity, the aliphatic alcohols used in the present invention do not include other alcohols such as ether alcohols and specifically does not include methylcellosolve. The aliphatic alcohol includes one or more of ethanol, propanol, isopropanol, 1-butanol, 2-butanol, or tertiary butanol, and most preferably is 1-butanol.

The presence of the non-hydrocarbon solvent in the hydrolytic process of the invention minimizes technical difficulties associated with previous process arrangements employing a hydrocarbon such as toluene as a solvent. The so improved process does not exhibit the difficulties associated with stirring or melting of solid potassium hydroxide, allows the hydrolytic reaction to proceed in a more controllable way and does not require careful control of the course of the reaction, namely of the heating regimen.

The co-solvent is a hydrocarbon of a boiling point from 50° C. to 150° C., such as one or more of benzene, toluene, xylene and cyclohexane, and is preferably toluene.

The hydrolyzing agent may be any alkali and can take the form of an alkali metal containing compound or salt. The hydrolyzing agent is preferably selected from one or more of the following: an alkali metal hydroxide, an alkali metal alkoxide or an alkali metal carbonate and is most preferably potassium hydroxide.

The hydrolysis preferably proceeds essentially in a solution. The solvent system is selected so that it, at least partially, dissolves the alkaline hydrolysing agent. In this manner, the alkali, namely the alkaline hydroxide, reacts in the hydrolytic reaction predominantly in a liquid phase, and, consequently, the effective concentration of the alkaline hydroxide is at desired level. As a result, the hydrolytic process according to the present invention generally requires milder reaction conditions and/or shorter time for achieving completion. The reaction proceeds essentially to completion whereby local overheating caused by the exothermic reactions on a solid surface is reduced, as are problems incumbent with stirring, formation of insoluble complexes and temperature control. The hydrolysis of paroxetine phenylcarbamate to paroxetine according to the present invention enables the reaction to be carried out in an easily controllable, robust and reproducible manner in industrial scale.

The amount of the co-solvent, relative to the solvent, is not specifically limited; it may vary from approx. 1:100 to approx. 1:1 (v/v), more typically from 1:10 to 1:1 such as about 1:2.5.

Concentration of the carbamate in the hydrolytic reaction mixture is not critical; advantageously however, it should be kept as high as possible, and it may reach more than 10%, e.g. 10–20% (w/w) if butanol/toluene is used as a solvent/co-solvent system.

The paroxetine carbamate of formula (3) is preferably provided by reacting N-methylparoxetine of formula (2)

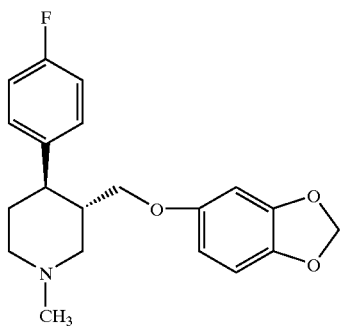

(2)

with a phenyl haloformate in a solvent, preferably being a hydrocarbon solvent, to form a mixture of the paroxetine phenylcarbamate of formula (3) and the solvent. The solvent may be any solvent that solubilizes the N-methylparoxetine, and preferably also is inert to the reaction with phenyl haloformate, is resistant to alkaline hydrolysis, is at least partly miscible with the solvent used for the hydrolysis and has a boiling point sufficiently high for the complete course of alkaline hydrolysis. Advantageously, such a solvent is a hydrocarbon of a boiling point from 50° C. to 150° C., such as benzene, toluene, xylene and cyclohexane, preferably toluene. Most preferably the hydrocarbon solvent is the co-solvent as referred to above, whereby this mixture can be subjected to the above referred to hydrolysis to provide the paroxetine.

Typically the solvent used in the production of the paroxetine phenylcarbamate, i.e. in the chemical reaction preceding the step of alkaline hydrolysis, is so selected that it does not interfere in that hydrolysis, thus it need not be removed after the reaction. Accordingly, the paroxetine can be formed from N-methylparoxetine without isolation of the phenylcarbamate intermediate; a procedure facilitating the ease and controllability of the reaction, especially on an economically acceptable, industrial scale. Thus, the time and energy consuming steps of solvent removal, isolation of the intermediate and/or its subsequent purification may be minimized in the process according to the present invention.

In a preferred embodiment, the paroxetine phenylcarbamate of formula (3) is prepared by a reaction of N-methylparoxetine of formula (2) and phenyl haloformate in the same inert co-solvent as used for the hydrolysis reaction in producing paroxetine according to the present invention. The mixture of paroxetine phenylcarbamate and the co-solvent, obtained as a result of the preceding reaction step, may be simply used for the subsequent hydrolytic reaction. The non-hydrocarbon solvent can be added with the hydrolyzing agent or separately.

Most preferably the non-hydrocarbon solvent is butanol, especially 1-butanol, and the hydrocarbon co-solvent is toluene.

The phenyl haloformate is preferably phenyl chloroformate, which is commercially available.

The starting N-methylparoxetine may be obtained by any of the prior art procedures, e.g. by a process outlined in U.S. Pat. No. 4,007,196, 4,902,801, or WO 00/26187. It may be used in crude or purified state, with or without the rest of the reaction or crystallization solvents.

In a preferred embodiment, the N-methylparoxetine is dissolved in toluene, and phenyl chloroformate is added to the resulting solution under stirring. If the N-methylparoxetine contains water, e.g. crystallization water, it is advantageous that water is removed prior the addition of phenyl chloroformate, e.g. by azeotropic distillation. The reaction temperature may vary from close to ambient to the boiling point of the mixture; the latter being preferred. A small amount of a base may be advantageously added, the base preferably being an organic amine, advantageously triethylamine. The by-product of the reaction is methyl chloride, which is gaseous at the reaction temperature and is liberated from the reaction mixture. The reaction vessel can thus be equipped with any suitable equipment for trapping the liberated methylchloride, e.g. a scrubber. After the reaction, the reaction mixture may advantageously be kept heated at increased temperature, e.g. at reflux for 0.5–3 hours to remove any methyl chloride. Completeness of the reaction may be checked by any suitable analytical method, e.g. by thin layer chromatography using reference samples of N-methylparoxetine and paroxetine phenylcarbamate. The reaction mixture may be further purified from the rest of reagents and side products by e.g. stirring with activated charcoal or silica gel, and also may be dried.

The obtained solution of paroxetine phenylcarbamate is then used in the alkaline hydrolysis. Preferably, the obtained solution may be concentrated by evaporation of a certain part of the solvent, advantageously to the highest possible concentration of paroxetine phenylcarbamate.

Alternatively, the paroxetine phenylcarbamate (3) may be used in the hydrolytic process of the invention in a solid, crude or a purified state. In this embodiment, it may be obtained by any known procedure, including the procedure outlined above.

In the hydrolytic process of the present invention, paroxetine phenylcarbamate (3) and, optionally, the inert co-solvent, are mixed with the non-hydrocarbon solvent, preferably butanol, and an alkali, preferably potassium hydroxide. In a preferred embodiment, the mixture of paroxetine phenylcarbamate solution and the co-solvent obtained in the above described preceded step is first diluted by the solvent to decrease the viscosity and then added to a pre-prepared mixture of the hydroxide with a next portion of the solvent. Preferably, the mixture of the alkaline hydroxide with the solvent is pre-heated, e.g. to 60–90° C., advantageously to obtain an essentially complete dissolution of the hydroxide in the solvent. Charging of the paroxetine phenylcarbamate solution may proceed at the same temperature and the speed of charging may be controlled by ordinary means. The hydrolytic reaction between carbamate and potassium hydroxide is exothermic; it may bring the reaction mixture into reflux spontaneously, without external heating. Even some cooling may be sometimes required for controlling the reaction rate and evolved heat. The hydrolytic reaction proceeds generally in a solution or in a thin suspension.

The amount of the co-solvent, relative to the solvent, is not specifically limited; it may vary from approx. 1:100 to approx. 1:1 (v/v), more typically 1:10 to 1:1 such as about 1:2.5 as is shown in Example 1 hereinafter. Concentration of the carbamate in the hydrolytic reaction mixture is not critical. Advantageously however, it should be kept as high as possible, and it may reach more than 10%, e.g. 10–20% (w/w) if 1-butanol/toluene is used as a solvent/co-solvent system, as there are generally no substantial problems with stirring of the reaction mixture in such a system.

The reaction course may be monitored by any suitable analytical technique, e.g. by thin layer chromatography using paroxetine and paroxetine phenylcarbamate as reference materials. The reaction may be regarded as complete if the amount of unreacted carbamate is less than 1% of the amount of paroxetine found. The necessary reaction time is preferably does not exceed 6 hours and is usually 1–3 hours, typically 2 hours.

After the reaction, the reaction mixture may be purified from the excess of alkali and from any undesired co-products comprising the cleaved phenoxycarbonyl moiety. A preferred treatment comprises washing (extraction) the hot reaction mixture with water, aqueous sodium hydroxide, aqueous sodium chloride and/or a combination of these. As butanol is partly soluble in water, it may be continuously replaced with fresh toluene during the washing procedures or, alternately, the toluene/butanol solvent may be completely removed by evaporation at reduced pressure and replaced with toluene which may be similarly washed. The obtained solution of paroxetine may be also further purified, e.g. by activated charcoal and/or silica gel and optionally dried.

Following washing, paroxetine may be isolated in a sufficiently pure form from the toluene solution by evaporation.

The process according to the present invention preferably comprises the further step of conversion of the paroxetine into a pharmaceutically acceptable acid addition salt such as paroxetine hydrochloride, paroxetine maleate or paroxetine mesylate, preferably into paroxetine mesylate, most preferably by treating a solution of the paroxetine in a solvent with methane sulfonic acid and recovering the paroxetine mesylate from the reaction mixture in the solid state.

A most preferred embodiment of the present invention is the production of paroxetine and/or pharmaceutically acceptable acid addition salts thereof, comprising contacting paroxetine phenylcarbamate with potassium hydroxide in butanol under reflux followed by recovery of paroxetine from the reaction mixture. The obtained product may be used for production of any known acid addition salt of paroxetine, particularly pharmaceutically acceptable acid addition salt, for instance for production of paroxetine mesylate, paroxetine hydrochloride, paroxetine maleate and others.

In the production of paroxetine mesylate, ethyl acetate or ethanol are the most suitable solvents for the salt formation. In an industrially suitable process, paroxetine obtained by the present process is dissolved in said solvent at increased temperature, preferably between 50° C. and 70° C. and methane sulphonic acid is added at the same temperature to the solution. The resulting solution is cooled to a temperature close to ambient, e.g. 20° C.–30° C., inoculated with a seeding crystal and cooled to about 0° C. After stirring at the same temperature for 0.5–3 hours, the solid product is filtered or centrifuged and washed with the same solvent. If necessary, the product may be recrystallized, advantageously from the same solvent.

Paroxetine obtained using this invention may be formulated for therapy in various dosage forms, either in solid formulations such as tablets or capsules or as solutions for oral or parenteral use, e.g. in those as described in EP 223403 or WO 96-24595.

Therapeutic uses of paroxetine and especially paroxetine mesylate obtained using this invention comprise treatment of depression and related disorders such as obsessive compulsive disorder, panic disorder, social phobia, generalized anxiety disorder, chronic pain, alcoholism, anxiety, obesity, senile dementia, migraine, bulimia, anorexia, pre-menstrual syndrome, substance abuse and similar disorders.

Accordingly, the present invention also provides a pharmaceutical composition for treatment or prophylaxis of the listed disorders comprising paroxetine or its pharmaceutically acceptable acid addition salt, particularly paroxetine mesylate, obtained using the process of this invention, and a pharmaceutically acceptable carrier. Further, it provides the use of paroxetine, its pharmaceutically acceptable acid addition salt(s) and particularly paroxetine mesylate, obtained using the process of this invention, for manufacturing a medicament for the treatment or prevention of the disorders listed. Yet further, it provides a method of treating the disorders listed which comprises administering an effective or prophylactic amount of paroxetine, its pharmaceutically acceptable acid addition salt(s) and particularly paroxetine mesylate, obtained using the process of this invention, to a person suffering from one or more of the disorders.

The invention is illustrated by the following Examples.

EXAMPLE I

Paroxetine Methane Sulfonate a) Paroxetine Phenylcarbamate

The reaction vessel was charged with 17.4 kg of N-methylparoxetine (containing approx. 5% of water) and 58 liter of toluene. The reaction mixture was heated to reflux and rests of water were removed by azeotropic distillation using a Dean-Stark receiver. Under reflux, 9.1 kg of phenyl chloroformate was added in 30 minutes and stirring continued at reflux for 1.5 hours. 0.8 liter of triethylamine was added and the mixture was heated under reflux for next 30 minutes. The solution was concentrated to approx. 30 liter volume by distillation at diminished pressure (30 mbar) and cooled to ambient temperature.

b) Paroxetine Free Base

The reaction vessel was charged with 16 kg of potassium hydroxide and 45 liters of 1-butanol and the mixture was heated under stirring to 80° C. The solution from the preceded step was mixed with 33 liters of 1-butanol and the combined solution was added to the above mixture under stirring. In approx. 20 minutes, the exothermic reaction brought the mixture spontaneously to reflux. Supply vessels and pipes were rinsed with next 5 liters of butanol which was combined with the reaction mixture. The reaction mixture was stirred under reflux for 2 hours. Then the mixture was cooled to approx. 95° C. and 45 liters of water was added under stirring. The mixture was allowed to stand for phase separation and the lower phase was discarded. The upper phase with diluted with 13 liters of toluene and the combined solution was washed with 19 kg of 30% aqueous NaOH solution and with 18 kg of 16% aqueous NaCl. The solvent was removed by distillation at reduced pressure at 50° C.

The crude product was dissolved in 70 liters of toluene, 0.3 kg of Tonsil was added and the reaction mixture was filtered. The reactor and filter were rinsed with next 5 liters of toluene. The combined toluene solution was washed twice with 35 liters of water and evaporated at reduced pressure at 50–60° C.

c) Paroxetine Mesylate

The product from the step b) was mixed with 58 liters of ethanol and heated to 60° C. Methane sulphonic acid (4.9 kg) was added to the resulted solution under stirring. The solution was cooled to 25° C. and inoculated with a seed crystal. The mixture was cooled to 0° C., stirred for 30 minutes and the obtained solid was filtered. The filter cake was washed with 2×6 kg of cold ethanol.

19.6 kg of wet paroxetine mesylate was obtained. After recrystallization from ethanol and drying, 14.5 kg of the dried product was obtained.

The invention having been thus described, it will be obvious to the worker skilled in the art that the same may be varied in many ways without departing from the spirit of the invention and all such modifications are included within the scope of the present invention as set forth in the following claims.

We claim:
1. A process for the production of paroxetine, which comprises hydrolyzing a paroxetine phenylcarbamate of formula (3)

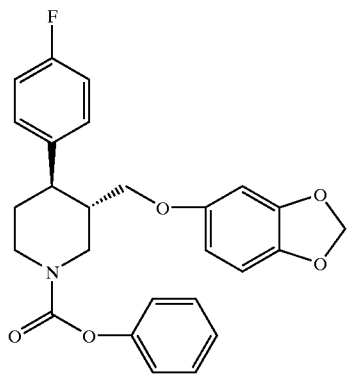

(3)

with a hydrolyzing agent in a solvent system comprising 1-butanol and a hydrocarbon co-solvent, to form a paroxetine compound of formula (1)

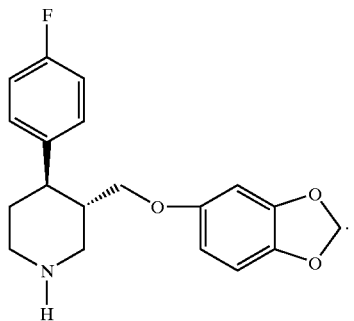

(1)

2. The process according to claim 1, wherein said hydrocarbon co-solvent is selected from the group consisting of benzene, cyclohexane, xylene, toluene, and combinations of two or more thereof.
3. The process according to claim 2, wherein said co-solvent is toluene.
4. The process according to claim 1, wherein the ratio of said 1-butanol to said co-solvent is within the range of 100–1:1 based on volume.
5. The process according to claim 4, wherein said solvent system comprises 1-butanol and toluene in a volume ratio of about 2.5:1.
6. The process according to claim 1, wherein said hydrolyzing agent is an alkali metal-containing compound.
7. The process according to claim 6, wherein said hydrolyzing agent is selected from the group consisting of an alkali metal hydroxide, an alkali metal alkoxide, an alkali metal carbonate, and combinations of two or more thereof.
8. The process according to claim 7, wherein said hydrolyzing agent is potassium hydroxide.
9. The process according to claim 1, wherein said hydrolyzing proceeds essentially in solution.
10. The process according to claim 1, which further comprises reacting N-methylparoxetine of formula (2)

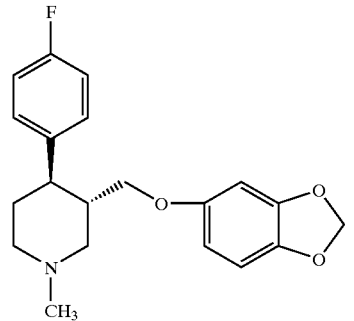

(2)

with a phenyl haloformate to form said paroxetine phenylcarbamate of formula (3).
11. The process according to claim 10, wherein said phenyl haloformate is phenyl chloroformate.
12. The process according to claim 11, wherein said N-methylparoxetine is reacted with said phenyl haloformate in a hydrocarbon solvent.
13. The process according to claim 11, wherein said hydrocarbon solvent is used in said solvent system as said co-solvent.
14. The process according to claim 13, wherein the mixture of N-methyl paroxetine, phenyl haloformate, and hydrocarbon solvent is substantially not subjected to any processing steps.

15. The process according to claim 13, wherein said paroxetine phenylcarbamate is not isolated before being subjected to said hydrolyzing reaction.

16. The process according to claim 1, which further comprises converting said paroxetine into a pharmaceutically acceptable acid addition salt thereof.

17. The process according to claim 16, wherein said pharmaceutically acceptable acid addition salt is paroxetine hydrochloride.

18. The process according to claim 16, wherein said pharmaceutically acceptable acid addition salt is paroxetine mesylate.

19. A process for the production of paroxetine and/or pharmaceutically acceptable acid addition salts thereof, which comprises contacting paroxetine phenylcarbamate of formula (3)

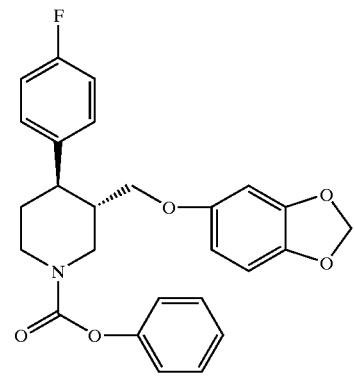

(3)

with potassium hydroxide in a butanol and toluene solvent under reflux to form paroxetine; recovering said paroxetine; and optionally exposing the paroxetine to a suitable acid.

20. The process according to claim 19, which further comprises contacting N-methylparoxetine with phenyl chloroformate in toluene under reflux conditions to form said paroxetine phenylcarbamate.

* * * * *